US011801225B2

(12) United States Patent
Ingram et al.

(10) Patent No.: US 11,801,225 B2
(45) Date of Patent: Oct. 31, 2023

(54) ORAL DOSAGE FORMS COMPRISING A HOPS EXTRACT

(71) Applicant: The New Zealand Institute for Plant and Food Research Limited, Auckland (NZ)

(72) Inventors: John Ronald Ingram, Auckland (NZ); Edward George Walker, Auckland (NZ)

(73) Assignee: THE NEW ZEALAND INSTITUTE FOR PLANT AND FOOD RESEARCH LIMITED, Auckland (NZ)

( * ) Notice: Subject to any disclaimer, the term of this patent is extended or adjusted under 35 U.S.C. 154(b) by 71 days.

(21) Appl. No.: 16/970,218

(22) PCT Filed: Apr. 23, 2018

(86) PCT No.: PCT/IB2018/052792
§ 371 (c)(1),
(2) Date: Aug. 14, 2020

(87) PCT Pub. No.: WO2019/158983
PCT Pub. Date: Aug. 22, 2019

(65) Prior Publication Data
US 2021/0077412 A1 Mar. 18, 2021

(30) Foreign Application Priority Data
Feb. 16, 2018 (AU) ................... 2018900489

(51) Int. Cl.
*A61K 9/48* (2006.01)
*A61K 9/00* (2006.01)
*A61K 31/122* (2006.01)
*A61K 36/185* (2006.01)

(52) U.S. Cl.
CPC .......... *A61K 9/4875* (2013.01); *A61K 9/0053* (2013.01); *A61K 9/4816* (2013.01); *A61K 31/122* (2013.01); *A61K 36/185* (2013.01)

(58) Field of Classification Search
CPC .. A61K 9/4875; A61K 9/0053; A61K 9/4816; A61K 31/122; A61K 36/185; A61P 3/04
See application file for complete search history.

(56) References Cited

U.S. PATENT DOCUMENTS

| 8,980,953 | B2 | 3/2015 | Taniguchi et al. | |
| 9,861,611 | B2 | 1/2018 | Bromley | |
| 2002/0086070 | A1* | 7/2002 | Kuhrts | A61K 38/39 |
| | | | | 424/773 |
| 2005/0101581 | A1* | 5/2005 | Reading | A61K 31/56 |
| | | | | 514/178 |
| 2006/0013870 | A1 | 1/2006 | Kuhrts | |
| 2009/0087512 | A1 | 4/2009 | Tripp et al. | |
| 2009/0186142 | A1 | 7/2009 | Tatewaki et al. | |
| 2013/0316068 | A1 | 11/2013 | Taniguchi et al. | |
| 2015/0197472 | A1 | 7/2015 | Dahlberg | |
| 2016/0081975 | A1* | 3/2016 | Bromley | A61K 31/12 |
| | | | | 514/168 |

FOREIGN PATENT DOCUMENTS

| CN | WO 1814094 A | 8/2006 | |
| DE | 102 55 481 A1 | 6/2004 | |
| GB | 510931 | 8/1939 | |
| NZ | 527902 B | 6/2005 | |
| WO | WO 1999/020289 A1 | 4/1999 | |
| WO | WO 2006/138253 A1 | 12/2006 | |
| WO | WO 2007/041499 A2 | 4/2007 | |
| WO | WO 2008/113177 A1 | 9/2008 | |
| WO | WO 2010/068693 A1 | 6/2010 | |
| WO | WO 2011/151285 A1 | 12/2011 | |
| WO | WO-2012094636 A2 * | 7/2012 | ........... A61K 31/137 |
| WO | WO 2016/178589 A1 | 11/2016 | |

OTHER PUBLICATIONS

Avau et al. (2016) "The bitter truth about bitter taste receptors: beyond sensing bitter in the oral cavity," Acta physiologica 216(4): 407-420.
Ivanova et. (2014) "Solid-state determination of hop bitter acids in beer by UV-MALDI-Orbitrap mass spectrometry," Food Measure 8: 343-355.
Ji et al. (2014) "Identification of novel compounds for human bitter taste receptors," Chemical biology & drug design, 84(1): 63-74.
Andreozzi et al. (2015) "The Bitter Taste Receptor Agonist Quinine Reduces Calorie Intake and Increases the Postprandial Release of Cholecystokinin in Healthy Subjects," J Neurogastroenterol Motil 21(4): 511-519.
Avau et al. (2015) "Targeting extra-oral bitter taste receptors modulates gastrointestinal motility with effects on satiation," Scientific Reports 5(1): 1-12.
Avau et al. (2016) "The bitter truth about bitter taste receptors: beyond sensing bitter in the oral cavity," Acta physiologica 216(4): 407-420 (abstract only).
Bowden, Jennifer (2016), available online at New Zealand Listener, issue 3975, Aug. 19, 2015, http://www.listener.co.nz/lifestyle/nutrition/plant-extract-weight-loss, 1 page.
Broughton (2016) "Plant extract hailed as key to fighting fat epidemic," available online at https://www.stuff.co.nz/life-style/well-good/teach-me/80711494/kiwi-plant-extract-hailed-as-key-to-fighting-fat-epidemic, 7 pages.

(Continued)

*Primary Examiner* — Robert A Wax
*Assistant Examiner* — Quanglong N Truong
(74) *Attorney, Agent, or Firm* — Leydig, Voit & Mayer, Ltd.

(57) ABSTRACT

This invention provides novel oral dosage forms comprising a hops extract. The oral dosage forms are capable of activating bitter taste receptors expressed in the gastrointestinal tract. The applications include but are not limited to the use of the oral dosage forms for reducing energy intake and/or appetite in a subject.

9 Claims, 5 Drawing Sheets

(56) References Cited

OTHER PUBLICATIONS

Chen et al. (2006) "Bitter stimuli induce Ca2+ signaling and CCK release in enteroendocrine STC-1 cells: role of L-type voltage-sensitive Ca2+ channels," Am J Physiol Cell Physiol, 291(4): C726-C739.
Clinical trial "The Effect of Bitter, Umami and Sweet Tastants on Food Intake," This study has been completed. Sponsor: Maastricht University Medical Center. ClinicalTrials.gov Identifier: NCT01956838, available online at https://clinicaltrials.gov/ct2/show/NCT01956838, 7 pages.
Daniells (2012) "Hop extract shows weight management potential," available online at https://www.nutraingredients-usa.com/Article/2012/09/26/Hop-extract-shows-weight-management-potential, 2 pages.
Deloose et al. (2013) "In Man Intragastric Administration of the Bitter Compound Denatonium Benzoate Decreases Hunger and the Occurrence of Gastric Phase III in the Fasting State," Gastroenterology, 144(5) Supplement 1: S-548.
Depoortere (2014) "Taste receptors of the gut: emerging roles in health and disease," Gut 63(1): 179-190.
Dotson et al. (2008) "Bitter Taste Receptors Influence Glucose Homeostasis," PLoS One 3(12): 10 pages.
Everard et al. (2012) "Tetrahydro iso-alpha acids from hops improve glucose homeostasis and reduce body weight gain and metabolic endotoxemia in high-fat diet-fed mice," PLoS One 7(3): 8 pages.
Green Flash Brewing Company (2017) "Green Flash Pacific Gem Single Hop Pale Ale," available online at https://www.ratebeer.com/beer/greenflashpacificgemsinglehoppaleale/363325, 4 pages.
Hautke et al. (1967) "The influence of environmental conditions on the proportions of cohumulone ashumulone and humulone in Hop a acids," Journal of the Institute of brewing 73: 51-59.
Ingram et al. (2012), "Foods for appetite control: Developing plant-based functional foods targeting satiety," Obesity Research & Clinical Practice 6(S1): 20 (abstract only).
Ingram et al. (2016) "A proprietary plant-based, functional ingredient, Amarasate™ extract, suppresses food intake and stimulates gastrointestinal peptide hormones in healthy men," 17(Suppl. 2): 21-34, Abstract No. T2:S10:20.
Intelmann et al. (2009) "Three TAS2R Bitter Taste Receptors Mediate the Psychophysical Responses to Bitter Compounds of Hops (*Humulus lupulus* L.) and Beer," Chem. Percept. 2: 118-132.
International Search Report and Written Opinion, dated Jul. 5, 2018, for International Application No. PCT/IB2018/052792 (filed Apr. 23, 2018).
Ivanova et. (2014) "Solid-state determination of hop bitter acids in beer by UV-MALDI-Orbitrap mass spectrometry," Food Measure 8: 343-355 (abstract only).
Jang et al. (2007) "Gut-expressed gustducin and taste receptors regulate secretion of glucagon-like peptide-1," PNAS 104(38), 15069-15074.
Janssen et al. (2011) "Bitter taste receptors and (alpha)-gustducin regulate the secretion of ghrelin with functional effects on food intake and gastric emptying," PNAS 108(5): 2094-2099.
Ji et al. (2014) "Identification of novel compounds for human bitter taste receptors," Chemical biology & drug design, 84(1): 63-74 (abstract only).
Johnston (2016) "Plant drug helps trim diet: study," available online at https://www.nzherald.co.nz/nz/plant-drug-helps-trim-diet-study/R6DELDQN5HUKO5GSNGDKAI6LEM, 3 pages.
Kaji et al. (2009) "Secretory effects of a luminal bitter tastant and expressions of bitter taste receptors, T2Rs, in the human and rat large intestine. American journal of physiology—Gastrointestinal and Liver Physiology," 296(5), G971-G981.
Kim et al. (2014) "Denatonium induces secretion of glucagon-like peptide-1 through activation of bitter taste receptor pathways," Diabetologia 57(10): 2117-2125.
Konda et al. (2014) "KDT501, a derivative from hops, normalizes glucose metabolism and body weight in rodent models of diabetes," PLoS One 9(1): p. e87848.
Latorre et al. (2016) "Expression of the Bitter Taste Receptor, T2R38, in Enteroendocrine Cells of the Colonic Mucosa of Overweight/Obese vs. Lean Subjects," PloS one 11 (2): 16 pages.
Le Nevé et al. (2010) "The steroid glycoside Hg-12 from Hoodia gordonii activates the human bitter receptor TAS2R14 and induces CCK release from HuTu-80 cells," American Journal of Physiology—Gastrointestinal and Liver Physiology 299: G1368-G1375.
Macrae (2016) "The bitter pill that dieters will be very keen to swallow: Substance found in plants can fool the body into believing it is full," available online at https://www.dailymail.co.uk/news/article-3623002/The-bitter-pill-dieters-keen-swallow-Substance-plants-fool-body-believing-full.html, 6 pages.
Meyerhof et al. (2010) "The molecular receptive ranges of human TAS2R bitter taste receptors," Chemical Senses 35 (2): 157-170.
Morimoto-Kobayashi et al. (2016) "Matured hop extract reduces body fat in healthy overweight humans: a randomized double blind, placebo-controlled parallel group study," Nutrition Journal 15:25: 13 pages.
Morimoto-Kobayashi et al. (2015) "Matured Hop Bittering Components Induce Thermogenesis in Brown Adipose Tissue via Sympathetic Nerve Activity," PLoS One, 10(6): 14 pages.
Nolden et al. (2016) "Differential bitterness in capsaicin, piperine, and ethanol associates with polymorphisms in multiple bitter taste receptor genes," Physiology & Behavior 156: 117-27.
Obara et al. (2009) "Isohumulones, the bitter component of beer, improve hyperglycemia and decrease body fat in Japanese subjects with prediabetes," Clinical Nutrition 28(3): 278-84.
Rozengurt et al. (2006) "Colocalization of the (alpha)-subunit of gustducin with PYY and GLP-1 in L cells of human colon," American Journal of Physiology—Gastrointestinal and Liver Physiology 291: G792-G802.
Sternini et al. (2008) "Enteroendocrine cells: a site of 'taste' in gastrointestinal chemosensing," Current Opinion in Endocrinology, Diabetes, and Obesity 15(1): 73-78.
Sumiyoshi et al. (2013) "Hop (*Humulus lupulus* L.) extract inhibits obesity in mice fed a high-fat diet over the long term," British Journal of Nutrition 109: 162-172.
University of California—Irvine (2008) "Small Intestine Can Sense and React to Bitter Toxins in Food," ScienceDaily <www.sciencedaily.com/releases/2008/10/081009185032.htm>.
Van Avesaat et al. (2015) "Intraduodenal infusion of a combination of tastants decreases food intake in humans," Am J Clin Nutr 102(4): 729-735.
Wang et al. (2014) "Bitter Taste Mediated Calcium Signaling in Enteroendocrine Cells," In: Goh J. (eds) The 15th International Conference on Biomedical Engineering. IFMBE Proceedings, vol. 43. Springer, Cham.
Wu et al. (2002) "Expression of bitter taste receptors of the T2R family in the gastrointestinal tract and enteroendocrine STC-1 cells," PNAS 99(4): 2392-2397.
Yajima et al. (2004) "Isohumulones, bitter acids derived from hops, activate both peroxisome proliferator-activated receptor alpha and gamma and reduce insulin resistance," J Biol Chem 279(32): 33456-33462.
Beatson et al. (1994) "Regional trial evaluation and cultivar selection of triploid hop hybrids", New Zealand Jouranl of Crop and Horticultural Science 22(1), pp. 1-6.
Extended European Search Report and Opinion dated Nov. 4, 2021 in corresponding European Patent Application No. 18906321.7.
Hautke et al. (1967) "The influence of environmental conditions on the proportions of cohumulone, adhumulone and humulone in hop (alpha) acids", Journal of the Institute of Brewing 73, pp. 51-59.

\* cited by examiner

Hutu-80 responses to alpha and beta acids isolated from NZ Hops Pacific Gem extract, AC130087-0

ORAL DOSAGE FORMS COMPRISING A HOPS EXTRACT

CROSS-REFERENCE TO RELATED APPLICATIONS

This application is a U.S. National Stage Application filed under 35 U.S.C. § 371 of International Application No. PCT/IB2018/052792, filed Apr. 23, 2018, which claims the benefit of Australian Application No. 2018900489, filed Feb. 16, 2018. Both of these applications are hereby incorporated by reference in their entireties.

FIELD OF THE INVENTION

The present invention generally relates to hops extracts in oral dosage forms and the use of the oral dosage forms for reducing energy intake and/or appetite.

BACKGROUND OF THE INVENTION

With over 2 billion people currently overweight or obese and predictions of almost half the world's adult population being overweight or obese by 2030, the need for effective weight management has never been greater.

Many nutraceutical products are marketed to people that want to lose weight. However, most of these products are not effective and many result in unpleasant side effects. For example, caffeine is a common ingredient in weight loss products. While caffeine can suppress appetite in some people, most users develop a tolerance to caffeine over time and high doses of caffeine are associated with insomnia, irritability and rapid heartbeat.

Hops extracts have also been included in weight loss products. However, previous investigation into the weight management benefit of hops extracts has focused on iso-acids, see for example META060 protects against diet-induced obesity and insulin resistance in a high-fat-diet fed mouse, Vroegrijk, Irene O. C. M. et al. Nutrition, Volume 29, Issue 1, 276-283. Iso-acids are an isomerised form of the native acids created when the acids from hops are heated during the brewing process. Iso-acids only activate TAS2R1 and TAS2R14, ie the isomerised forms do not activate TAS2R40. Furthermore, the primary target of isomerised acids is TAS2R1. However, this receptor is not present in all individuals and has not been detected in the enteroendocrine cell lines used for screening. In addition, isomerised acids taste more bitter as TAS2R1 is also an oral receptor. The bitterness is off-putting to some consumers.

Hops extracts are also known to be used for purposes unrelated to weight management, eg as sleep aids. Hops extracts prepared for non-weight management purposes are commonly prepared in powder form to avoid nausea and other undesired side effects associated with oral delivery of hops extracts.

Accordingly, it is an object of the present invention to go some way to avoiding the above disadvantages; and/or to at least provide the public with a useful choice. Other objects of the invention may become apparent from the following description which is given by way of example only.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date.

SUMMARY OF THE INVENTION

Enhancement of satiety may play an important role in increasing compliance during dieting or fasting and thereby promoting successful weight management. In particular, activation of specific bitter taste receptors (TAS2Rs), expressed throughout the gastrointestinal (GI) tract by enteroendocrine cells, can modulate feeding behaviour via release of gut peptide hormones involved in the regulation of GI function and appetite e.g. cholecystokinin (CCK) and glucagon-like peptide 1 (GLP-1).

Although previous studies have detected the presence of TAS2Rs within the human gastrointestinal tract (Kaji et al., 2009; Le Neve et al., 2010; Rozengurt et al., 2006; Wu et al., 2002), these studies have been somewhat limited in their scope and have not allowed for the detailed mapping that is conducive to understanding chemosensory systems and inferring potential physiological responses.

Work by the inventors has established the existence of TAS2Rs in the gastrointestinal (GI) tract. The inventors have also found that TAS2R14 and TAS2R40 are detectable in the gut tissue of all tested subjects, whereas TAS2R1 was only detectable in some individuals. Without wishing to be bound by theory, the applicants currently believe that binding hops extracts to TAS2R40 and TAS2R14 are important in the weight management mechanism. Binding to TAS2R1 currently appears less important particularly where that receptor is an oral receptor and is not found in the gut tissue of all tested subjects.

Hops extracts (*Humulus lupulus*) are known to be bitter and capable of activating TAS2Rs in mouth, particularly TAS2R1, TAS2R14 and TAS2R40, see Three TAS2R Bitter Taste Receptors Mediate the Psychophysical Responses to Bitter Compounds of Hops (*Humulus lupulus* L.) and Beer, Intelmann, D., Batram, C., Kuhn, C. et al. Chem. Percept. (2009) 2: 118.

The inventors believe that extracts from hops can be used to modify energy intake, subjective ratings of appetite and gut peptide hormone concentrations. Without wishing to be bound by theory, the inventors believe it is the specific components of the hops extract, e.g. alpha acids such as humulone, cohumulone, adhumulone, beta acids such as lupulone, colupulone and adlupulone and prenylated flavonoids such as xanthohumol that are capable of activating the TAS2Rs, particular TAS2R40 and TAS2R14, in the GI tract. Alpha acids are currently believed to play a prominent role in activating the receptors TAS2R40 and TAS2R14 in the GI tract.

In particular, the inventors believe that cohumulone is one of the strongest active compounds for stimulating gut peptide hormone release from gut enteroendocrine cells. As the enteroendocrine cell-lines used in the present invention appear not to express TAS2R1, the inventors believe that cohumulone may act primarily through activating the bitter taste receptor TAS2R40. Without wishing to be bound by theory it is also believed that the presence of small amounts of other alpha and beta acids in the hops extract may work on other receptors, resulting in a synergistic effect.

Accordingly, in one aspect the invention provides a delayed release oral dosage form comprising a hops extract, wherein the acid component of the hops extract is not isomerised. In one embodiment, less than 40%, less than 30%, less than 20%, less than 10%, less than 5%, preferably less than 2% of the acid component of the hops extract is isomerised.

In another aspect, the invention provides an oral dosage form comprising a hops extract, wherein the acid component of the hops extract comprises 25-100% w/w alpha-acids.

In one embodiment the acid component of the hops extract comprises 30-65% w/w alpha-acids. In one embodiment the acid component of the hops extract comprises 40-55% w/w alpha-acids. In one embodiment the acid component of the hops extract comprises greater than 50% w/w alpha acids.

In another aspect, the invention provides an oral dosage form comprising a hops extract, wherein the alpha acid component of the hops extract comprises 10-45% w/w cohumulone, preferably 15-25% w/w cohumulone, preferably about 18-22% w/w cohumulone, more preferably about 20% w/w cohumulone.

In one embodiment the oral dosage form comprises 5-200 mg cohumulone. In one embodiment the oral dosage form comprises 10-100 mg cohumulone. In one embodiment the oral dosage form comprises 20-50 mg cohumulone.

In one embodiment the oral dosage form of the invention comprises 5-1000 mg of hops extract. In one embodiment the oral dosage form comprises 10-800 mg of hops extract. In one embodiment the oral dosage form comprises 20-600 mg of hops extract. In one embodiment the oral dosage form comprises 30-500 mg of hops extract. In one embodiment the oral dosage form comprises 40-400 mg of hops extract. In one embodiment the oral dosage form comprises 50-250 mg of hops extract. In one embodiment the oral dosage form comprises about 50 mg of hops extract. In one embodiment the oral dosage form comprises about 100 mg of hops extract. In one embodiment the oral dosage form comprises about 250 mg of hops extract. In one embodiment the oral dosage form comprises about 500 mg of hops extract.

In one embodiment the hops extract is from the cultivar Pacific Gem.

In one embodiment the hops extract is a $CO_2$ supercritical extract.

In one embodiment the oral dosage form further comprises an edible oil. Preferably the edible oil is canola oil.

In one embodiment the ratio of edible oil to hops extract is from 10:1 to 1:10. In one embodiment, the ratio of edible oil to hops extract is from 2:1 to 1:2. Preferably the ratio of edible oil to hops extract is about 1:1 or about 4:1.

In one embodiment the oral dosage form further comprises an antioxidant. Preferably the antioxidant is an edible oil. In one embodiment the edible oil is different to the antioxidant edible oil. More preferably the antioxidant edible oil is rosemary oil. In another embodiment the antioxidant is a rosemary extract.

In one embodiment the oral dosage form further comprises a viscosity modifier. Preferably the viscosity modifier is silicon dioxide.

In one aspect, the invention provides a delayed release oral dosage form comprising a single active component, wherein the active component consists essentially of cohumulone.

In one embodiment the oral dosage form is a delayed release capsule. In one embodiment the delayed release capsule is a Capsugel DRcaps capsule. In one embodiment the delayed release capsule is a Capsugel Licaps capsule.

In one embodiment the contents of the oral dosage form has a viscosity between 250 cP and 8000 P. In one embodiment the contents of the oral dosage form has a viscosity between 1 P and 3000 P. In one embodiment the contents of the oral dosage form has a viscosity between 500 P and 2000 P.

In another aspect the invention provides an oral dosage form comprising:
a) 100 mg of a supercritical $CO_2$ hops extract from the cultivar Pacific Gem
b) approximately 492 mg canola oil
c) 1 mg rosemary oil and
d) optionally silicon dioxide
wherein the oral dosage form is a Capsugel DRcaps capsule.

In another aspect the invention provides an oral dosage form comprising:
a) 250 mg of a supercritical $CO_2$ hops extract from the cultivar Pacific Gem
b) approximately 342 mg canola oil
c) 1 mg rosemary oil and
d) optionally silicon dioxide
wherein the oral dosage form is a Capsugel DRcaps capsule.

In another aspect the invention provides an oral dosage form comprising:
a) 100 mg of a supercritical $CO_2$ hops extract from the cultivar Pacific Gem
b) approximately 492 mg canola oil
c) 1 mg rosemary oil and
d) optionally silicon dioxide
wherein the oral dosage form is a Capsugel Licaps capsule.

In another aspect the invention provides an oral dosage form comprising:
a) 250 mg of a supercritical $CO_2$ hops extract from the cultivar Pacific Gem
b) approximately 342 mg canola oil
c) 1 mg rosemary oil and
d) optionally silicon dioxide
wherein the oral dosage form is a Capsugel Licaps capsule.

In another aspect the invention provides an oral dosage form comprising:
(a) 100 mg of a supercritical $CO_2$ hops extract from the cultivar Pacific Gem
(b) approximately 400 mg canola oil
(c) 1 mg rosemary oil and
(d) optionally silicon dioxide
wherein the oral dosage form is a Capsugel DRcaps capsule.

In another aspect the invention provides an oral dosage form comprising:
(a) 250 mg of a supercritical $CO_2$ hops extract from the cultivar Pacific Gem
(b) approximately 250 mg canola oil
(c) 1 mg rosemary oil and
(d) optionally silicon dioxide
wherein the oral dosage form is a Capsugel DRcaps capsule.

In another aspect the invention provides an oral dosage form comprising:
(a) 100 mg of a supercritical $CO_2$ hops extract from the cultivar Pacific Gem
(b) approximately 400 mg canola oil
(c) 1 mg rosemary oil and
(d) optionally silicon dioxide
wherein the oral dosage form is a Capsugel Licaps capsule.

In another aspect the invention provides an oral dosage form comprising:
(a) 250 mg of a supercritical $CO_2$ hops extract from the cultivar Pacific Gem
(b) approximately 250 mg canola oil
(c) 1 mg rosemary oil and
(d) optionally silicon dioxide
wherein the oral dosage form is a Capsugel Licaps capsule.

In another aspect the invention provides a method of reducing energy intake by a subject, comprising administering an oral dosage form according to the invention to the subject.

In another aspect the invention provides a method of
(a) reducing appetite
(b) increasing satiety hormones
(c) weight management
(d) appetite control
(e) decreasing food intake
(f) inducing satiety and/or
(g) treating obesity
comprising administering an oral dosage form according to the invention to the subject.

In another aspect the invention provides a method of losing weight comprising administering an oral dosage for according to the invention to a subject. In one embodiment, the subject loses weight through decreased energy intake and improved appetite control.

In one embodiment the oral dosage form is administered to the subject at least one hour before meal time. In one embodiment the oral dosage form is administered to the subject between one and three hours before meal time.

In one embodiment the oral dosage form is administered to provide 50-1000 mg of extract to the subject per day. In one embodiment the oral dosage form is administered to provide 100-800 mg of extract to the subject per day. In one embodiment the oral dosage form is administered to provide 200-600 mg of extract to the subject per day. In one embodiment the oral dosage form is administered to provide 200 mg or 500 mg of extract to the subject per day. The oral dosage forms may be administered as either a single daily dose or divided doses throughout the day. For example, in one embodiment a subject may take two dosage forms comprising 100 mg of hops extract per day. In another embodiment, a subject may take two dosage forms comprising 250 mg of hops extract per day.

In one embodiment the subject is following an intermittent fasting protocol.

In one aspect the invention relates to the use of a supercritical $CO_2$ hops extract from the cultivar Pacific Gem, an edible oil, an antioxidant and optionally silicon dioxide in the manufacture of an medicament for
(a) reducing energy intake
(b) reducing appetite
(c) increasing satiety hormones
(d) weight management
(e) appetite control
(f) decreasing food intake
(g) inducing satiety, and/or
(h) treating obesity
wherein the medicament is in the form of a Capsugel DRcaps capsule.

In one aspect the invention relates to the use of a supercritical $CO_2$ hops extract from the cultivar Pacific Gem, an edible oil, an antioxidant and optionally silicon dioxide in the manufacture of an medicament for
(a) reducing energy intake
(b) reducing appetite
(c) increasing satiety hormones
(d) weight management
(e) appetite control
(f) decreasing food intake
(g) inducing satiety, and/or
(h) treating obesity
wherein the medicament is in the form of a Capsugel Licaps capsule.

In one aspect, the invention provides a method of reducing energy intake by a subject comprising administering an agent capable of binding TAS2R1, TAS2R14 and TAS2R40 in the gastrointestinal tract of the subject.

In one aspect, the invention provides a method of reducing energy intake by a subject comprising administering a hops extract to the subject, wherein the acid component of the hops extract is not isomerised.

In one aspect, the invention provides a method of extending a period of fasting comprising administering an oral dosage form according to the invention to the subject.

In one aspect, the invention provides a method of reducing appetite during a period of fasting comprising administering an oral dosage form according to the invention to the subject.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

DEFINITIONS

The term "comprising" as used in this specification and claims means "consisting at least in part of". When interpreting statements in this specification and claims which include the term "comprising", other elements besides the elements prefaced by this term in each statement can also be present. Related terms such as "comprise" and "comprised" are to be interpreted in similar manner.

The phrase "consisting essentially of" will be understood to include those elements specifically recited and those additional elements that do not materially affect the basic and novel characteristics of the claimed technology. The phrase "consisting of" excludes any element not specified.

As used herein, the term "delayed release" means that release of the active ingredient in the hops extract is delayed until the dosage form has passed through the stomach. Preferably release of the active ingredient is delayed until the dosage form reaches the small intestine, more preferably the duodenum.

The term "effective amount" is an amount which produces a result or exerts an influence on energy intake, appetite, satiety hormones, weight management, appetite control, food intake, satiety and/or obesity in a subject. The effective amount may vary based on the age, weight, metabolism, sex, relative health and receptor expression of the subject. In particular, an effective amount is an amount sufficient to
a) reduce energy intake
b) reduce appetite
c) increase satiety hormones
d) manage weight
e) control appetite
f) decrease food intake
g) induce satiety, and/or
h) treat obesity
in a subject.

For convenience, the term "energy intake" is used herein to refer to either energy intake per se, or as shorthand reference for any of appetite, satiety hormones, weight management, appetite control, food intake, satiety and/or obesity as discussed above.

The term "pharmaceutically acceptable" as used herein, means approved by a Government regulatory agency for use in animals, in particular, humans. The excipient must be compatible with the other ingredients of the formulation and not harmful to the subject to whom the composition is administered.

The term "subject" as used herein includes humans, horses, dogs, cats, pigs, sheep, cattle, and goats but is not limited thereto. Preferably, the individual is a human.

DETAILED DESCRIPTION

The inventors have discovered that providing a hops extract with high cohumulone and/or high alpha acid content to the duodenum can reduce energy intake. Without wishing to be bound by theory it is believed that the hops extract works by binding certain TAS2Rs in the gut of a subject, particularly TAS2R40 and TAS2R14 in the small intestine and colon. Generally TAS2Rs are found throughout the gastrointestinal (GI) tract, including the small intestine. However, the hormone system triggered by the receptor is different depending on which part of the GI tract the receptor is located. The appetite suppression hormone connection is located in the small intestine and colon. In particular, targeting the receptors in the small intestine stimulates the release of CCK, and targeting receptors in the colon stimulates the release of GLP-1 and PYY. In contrast, activating the same receptors in the stomach may result in increased appetite, eg by stimulating ghrelin release.

To target the appropriate region of the gut, the hops extract needs to be in an oral release form, preferably a delayed release form. Once released, the active components in the hops extract bind to the TAS2R receptors and stimulate the release of several appetite suppressing gut peptide hormones including, CCK, GLP-1 and PYY.

Accordingly, in one aspect the invention provides a delayed release oral dosage form comprising a hops extract, wherein the acid component of the hops extract is not isomerised.

In another aspect, the invention provides an oral dosage form comprising a hops extract, wherein the acid component of the hops extract comprises 25-100% w/w alpha acids, preferably 30-65%, preferably 40-55% w/w alpha acids. In one embodiment the hops extract comprises greater than 50% w/w alpha acids.

The hops extract suitable for use in the invention can be obtained from the flowers of any cultivar with a high alpha acid or high cohumulone content. Alpha acids are compounds found in the flower of the hop plants. Common alpha acids include humulone, adhumulone, cohumulone, posthumulone and prehumulone. A person skilled in the art can readily analyse a hops extract to determine the alpha acid content and/or cohumulone content using, for example by using an HPLC base method as described in European Brewery Convention. 1998. Iso α-, α- and β-acids in hop and isomerized hop extracts by HPLC. Section 7 Method 7.8, p. 1-4. In EBC analysis Committee (ed.), Analytica-EBC, 5th ed. Verlag Hans Carl Getranke-Fachverlag: Nürnberg, Germany. 7. European Brewery Convention. 1998. Other suitable methods for determining the alpha acid content and/or cohumulone content of a hops extract, including NMR spectroscopy and mass spectroscopy, are known to the person skilled in the art.

In some embodiments the hops extract is from a cultivar selected from the group consisting of Pacific Gem, Admiral, Newport, Columbus and Sticklebract.

In one embodiment, the hops extract is from the cultivar Pacific Gem. "Pacific Gem" as used herein means the hops variety with the varietal code 79-32.

In one embodiment, the hops extract is from the cultivar Admiral. "Admiral" as used herein means the hops variety protected as European plant variety number 1436.

In one embodiment, the hops extract is from the cultivar Newport.

In one embodiment, the hops extract is from the cultivar Sticklebract.

In one embodiment, the hops extract is from the cultivar Columbus. "Columbus" as used herein means the hops variety protected as European plant variety number 11647 or US plant patent 10956.

Commercially available sources of hops extracts suitable for use in the invention include New Zealand Hops (Nelson, New Zealand) and Hopsteiner (New York, USA).

In one embodiment, the cohumulone content of the alpha acid component of the hops extract is about 10-45%, in another embodiment, the cohumulone content of the alpha acid component of the hops extract is about 15-25%, in another embodiment, the cohumulone content of the alpha acid component of the hops extract is about 12-22%, in another embodiment, the cohumulone content of the alpha acid component of the hops extract is about 20%. In another embodiment, the oral dosage form comprises 5-200 mg cohumulone, preferably 10-100 mg cohumulone, more preferably about 20-50 mg cohumulone.

In another embodiment the hops extract is enriched for alpha acids and/or cohumulone content. For example, in one embodiment the acid component of the hops extract is enriched so that the extract comprises 25-100% w/w alpha acids, preferably 30-65%, preferably 40-55% w/w alpha acids. In one embodiment the hops extract is enriched so that it comprises greater than 50% w/w alpha acids. In another embodiment, the hops extract is enriched so that the cohumulone content of the alpha acid component of the hops extract is about 10-45%, in another embodiment, the cohumulone content of the alpha acid component of the hops extract is about 15-25%, in another embodiment, the cohumulone content of the alpha acid component of the hops extract is about 12-22%, in another embodiment, the hops extract is enriched so that the cohumulone content of the alpha acid component of the hops extract is about 20%. Methods for enriching the alpha acid and/or cohumulone content of a hops extract are known to those skilled in the art, including for example the use of organic solvents, microwave systems, and super critical CO extraction.

In one embodiment the hops extract is not isomerised. In the context of the present invention, a hops extract is not isomerised if less than 50%, preferably less than 40%, less than 30%, less than 20%, less than 10%, less than 5%, preferably less than 2% of the acid component of the hops extract is isomerised. Non-isomerised acids are preferred because as a whole (i.e alpha and beta acids) they can activate all three TAS2Rs that are responsive to hops compounds.

In one embodiment the oral dosage form of the invention comprises 5-1000 mg of hops extract, preferably 10-800 mg, preferably 20-600 mg, preferably 30-500 mg, preferably 40-400 mg, preferably 50-250 mg, preferably 50 mg, preferably 100 mg, preferably 250 mg, or preferably 500 mg.

The amount of a hops extract that will be effective to reduce a subject's energy intake will vary depending on the cultivar used to produce the hops extract. The effective amount may also depend on factors specific to the subject such as their sex, age, weight, metabolism, relative health and receptor expression.

The hops extract of the invention is readily prepared using conventional processing techniques. In one embodiment, a hops extract suitable for use in the invention can be obtained using any extraction process that concentrates the alpha-acids present in hops, including but not limited to standard and high pressure solvent extractions using hexane, dimethylether, ethyl acetate, acetone, ethanol, methanol, toluene, water, oils, compressed gas, supercritical fluid or combination thereof. Extraction methodologies may include but are not limited to ultrasonic extraction, reflux extraction, Soxhlet Extraction, Accelerated Solvent Extractions (ASE) using temperature and pressure, distillations (vacuum or atmospheric pressure), enzyme-assisted extraction, microwave-assisted extraction and pulsed electric field (PEF) assisted extraction, acid-base extraction including derivatives of this method using chelation, and solid-Phase extraction.

Suitable methods for preparing a hops extract for use in the invention are also known in the art, for example
  Gardner D. S. (1993) Commercial scale extraction of alpha-acids and hop oils with compressed $CO_2$. In: King M. B., Bott T. R. (eds) Extraction of Natural Products Using Near-Critical Solvents. Springer, Dordrecht;
  Čulík, J., Jurková, M., Horák, T., Čejka, P., Kellner, V., Dvořák, J., Karásek, P. and Roth, M. (2009), Extraction of Bitter Acids from Hops and Hop Products Using Pressurized Solvent Extraction (PSE). Journal of the Institute of Brewing, 115: 220-225;
  R Donley, James (1992). Solid-Phase Extraction of Hop Acids from Beer or Wort for Subsequent Analysis. Journal of the American Society of Brewing Chemists. Vol 50 No. 3 p 89-93.

In some embodiments, the hops extract is a supercritical $CO_2$ extract or a solvent extract. A supercritical $CO_2$ extract can be prepared using standard techniques known to the skilled person. In one embodiment, liquid carbon dioxide is compressed and heated until it is at the desired extraction conditions above 32° C. and 72 bar—the critical point for $CO_2$. Extraction conditions range up to 500 bar and 120° C. depending on the extraction plant. This fluid is circulated through the matrix until the soluble hops extract material is removed. The carbon dioxide is reduced in pressure and temperature and recovered for use within the same extraction job. New $CO_2$ is used for each new extraction job. The extracted solids are then removed from the process and either become a secondary product or are disposed of appropriately. The resulting hops extract is a viscous or solid paste, golden green brown, consisting of the alpha-acids, beta-acids and hops oils, and other hops substances.

In some embodiments, the extract is prepared using solvent extraction. A hops extract can be prepared using standard solvent extraction techniques known to the skilled person. In one embodiment ethanol is used as the solvent.

In one aspect, the invention provides a delayed release oral dosage form comprising a single active component, wherein the active component consists essentially of cohumulone. Cohumulone can be obtained commercially from chemical suppliers, prepared by purification from hops or obtained by chemical synthesis. Various standard synthetic methods and techniques, including but not limited to synthetic chemistry transformations and protecting group based methods, allows for the chemical synthesis of cohumulone from available chemicals by those skilled in the art. Synthetic chemistry methodologies useful in synthesising cohumulone include those described in M. Verzele and D. De Keukeleire, Chemistry and Analysis of Hop and Beer Bitter Acids, Elsevier: Amsterdam (1991) and T. W. Greene and P. G. M. Wuts, Protective Groups in Organic Synthesis, 2nd ed., John Wiley and Sons (1991). Synthesized cohumulone can be isolated from the synthesis reaction by a variety of methodologies, including but not limited to HPLC and recrystallization. Methodologies for the chemical synthesis of cohumulone may be performed in an alternative order and/or using alternative methodologies, as may be understood by a person skilled in the art. In one embodiment, cohumulone can be isolated from a hops extract using a fractionation process as described below in Example 4.

In one embodiment the delayed release oral dosage form also includes a pharmaceutically acceptable carrier. Suitable carriers are known to the skilled person and include silica gel and magnesium stearate.

Oral dosage forms may be prepared by combining the hops extract with at least one pharmaceutically acceptable excipient suitable for use in solid oral dosage forms. The product is then shaped into the desired dosage form, for example by compression or molding.

Suitable excipients include but are not limited to diluents, granulating agents, wetting agents, suspending agents, fillers, lubricants, binders, solvents, glidants, preservatives, flavourings, colourings, sweeteners and disintegrating agents.

The skilled person is capable of selecting appropriate excipients depending of the type of oral dosage form being manufactured. For example, fillers include, but are not limited to talc, calcium carbonate granules or powder, microcrystalline cellulose, powdered cellulose, kaolin, mannitol, sorbitol and starch. Lubricants include but are not limited to calcium stearate, light mineral oil, glycerin, sorbitol, mannitol, polyethylene glycol, sodium lauryl sulfate, hydrogenated vegetable oil and agar. Wetting agents include but are not limited to lecithin and polyoxyethylene stearate. Suspending agents include but are not limited to sodium carboxymethylcellulose, methylcellulose and sodium alginate.

Generally, the dosage form needs to be of a type which permits delayed release of the hops extract until the dosage form reaches the small intestine. Suitable oral dosage forms and delayed release dosage forms are known in the art. We refer to Remington's Pharmaceutical Sciences, Allen, et al., 22nd Ed. ISBN 978-0-85711-062-6. Examples of dosage forms include, but are not limited to, tablets, capsules (both hard gelatin capsules and soft gelatin capsules), pills, pellets, capsules containing liquids, troches, dragees, pastilles and lozenges.

The oral dosage form is preferably prepared as a delayed release form. Delayed release forms are known in the art, for example multilayer forms in which the active hops extract is contained in an inner layer, or a coated form in which the hops extract is held inside a protective coating. Preferably the delayed release dosage form provides delivery of the extract to the duodenum.

In another embodiment, the oral dosage form may be a capsule. Hard or soft form capsules are possible. In one embodiment the oral dosage form is a delayed release capsule, for example a DRcaps capsule from Capsugel as described in WO 2011/036601 published 31 Mar. 2011. In one embodiment the capsule is banded. In this context, "banded" means the capsule is sealed. For example, once the capsule is filled and the capsule parts have been joined, banding may be carried out using gelatin or HPMC (hydroxypropylmethyl cellulose) to seal the joint between the capsule parts. DRcaps are HPMC (hydroxypropylmethyl cellulose) capsules which are gastric-resistant and mostly disintegrate in the small intestine. DRcaps capsules start to release at the distal end of the stomach after about 45 minutes.

Capsugel DRcaps capsules provide several advantages over other dosage forms, including
a) reduced side effects as compared to stomach delivery. For example, side effects associated with stomach delivery of hops can include nausea, gastric discomfort, eructation, stomach rumbling, loose stool and/or bloating.
b) ensures that the appetite suppressant hormones are released in time to reduce food intake (if the capsule is taken an hour before a meal).
c) improved bioaccessibility and dispersal of the active component. Because the active component is in liquid form it disperses in the GI tract and can target the TAS2R receptors more easily than a non-liquid formulation.

In one embodiment the oral dosage form is a Flofit hard gelatin banded capsule from ACG North America in the United States.

In one embodiment the oral dosage form is a Licaps Liquid-Filled Capsule from Capsugel as described in U.S. Pat. No. 8,377,471B2 or U.S. Pat. No. 8,715,722B2. Licaps capsules are HPMC (hydroxypropylmethyl cellulose) capsules.

In one embodiment the oral dosage form comprises a size 0 capsule. Other capsule sizes may be used and the skilled person can select an appropriate size based on the amount of hops extract, oil and other components to be encapsulated. For example, size 00 or size 1 capsules may be used.

The capsule may contain surfactants, lubricants, and inert fillers such as lactose, sucrose, calcium phosphate, and corn starch. The capsule may have the active in solid form (eg granules), inside the capsule. In another embodiment, the capsule may have the active in a liquid form inside the capsule. For example, an oily suspension may be formulated by suspending the hops extract in an edible oil. Alternatively, the hops extract and oil could be combined as an emulsion.

In one embodiment, the hops and oil mixture can be made by adding the required weight of edible oil to a hops extract and mixing the components until a homogeneous suspension is obtained.

Accordingly, in one embodiment the oral dosage form comprising a capsule comprises an edible oil. Suitable edible oils are known to the skilled person. In one embodiment the edible oil is safe for human consumption and relatively stable. The oil may be selected from the group consisting of canola, flaxseed, corn, soybean, mineral, safflower, sesame, coconut, avocado, peanut and olive oil. A mineral oil such as liquid paraffin could also be used. Canola oil is currently preferred.

In one embodiment the ratio of edible oil to hops extract is from 10:1 to 1:10. In one embodiment, the ratio of edible oil to hops extract is from 5:1 to 1:5. In one embodiment, the ratio of edible oil to hops extract is about 1:1 or about 4:1.

The mixture may also contain one or more preservatives, for example, ethyl or n-propyl p-hydroxybenzoate; one or more colouring agents; one or more flavouring agents; and one or more sweetening agents such as sucrose or saccharin. In one embodiment, a preservative is added to the hops extract and oil mixture.

In one embodiment, the preservative is an antioxidant, added to prevent oxidation of the oil and hops extract. Any suitable antioxidant may be used, for example in one embodiment the antioxidant is a second edible oil. In one embodiment, the edible oil and antioxidant edible oil are different edible oils. Rosemary oil is currently preferred. Other preservatives include Vitamin E, butylated hydroxyanisole (BHA), butylated hydroxytoluene (BHT), propyl gallate (PG), tert-Butylhydroquinone (TBHQ) but are not limited thereto.

In one embodiment, a viscosity modifier is added to the hops extract and oil mixture. For example, in one embodiment silicon dioxide is added to achieve suitable viscosity of the final formula. In one embodiment corn starch is added to achieve suitable viscosity of the final formula. A thickening agent such as, for example, beeswax, hard paraffin, or cetyl alcohol may also be used with the hops and oil mixture to modify viscosity. A suitable viscosity refers to the viscosity of the formulation being chosen to allow the hops extract to distribute throughout the duodenum without clumping. In one embodiment, the viscosity of the formulation is greater than 250 cP and less than 8000 P. In one embodiment the contents of the oral dosage form has a viscosity of greater than 1 P and less than 3000 P. In one embodiment the contents of the oral dosage form has a viscosity of greater than 500 P and less than 2000 P.

In one embodiment, the oral dosage form comprises:
(a) 100 mg of a supercritical $CO_2$ hops extract from the cultivar Pacific Gem
(b) approximately 492 mg canola oil
(c) 1 mg rosemary oil and
(d) optionally silicon dioxide
wherein the oral dosage form is a Capsugel DRcaps capsule.

In one embodiment, the oral dosage form comprises:
(a) 250 mg of a supercritical $CO_2$ hops extract from the cultivar Pacific Gem
(b) approximately 342 mg canola oil
(c) 1 mg rosemary oil and
(d) optionally silicon dioxide
wherein the oral dosage form is a Capsugel DRcaps capsule.

In one embodiment, the oral dosage form comprises:
(a) 100 mg of a supercritical $CO_2$ hops extract from the cultivar Pacific Gem
(b) approximately 492 mg canola oil
(c) 1 mg rosemary oil and
(d) optionally silicon dioxide
wherein the oral dosage form is a Capsugel Licaps capsule.

In one embodiment, the oral dosage form comprises:
(a) 250 mg of a supercritical $CO_2$ hops extract from the cultivar Pacific Gem
(b) approximately 342 mg canola oil
(c) 1 mg rosemary oil and
(d) optionally silicon dioxide
wherein the oral dosage form is a Capsugel Licaps capsule.

In one embodiment, the oral dosage form comprises:
(a) 100 mg of a supercritical $CO_2$ hops extract from the cultivar Pacific Gem
(b) approximately 400 mg canola oil
(c) 1 mg rosemary oil and
(d) optionally silicon dioxide
wherein the oral dosage form is a Capsugel DRcaps capsule.

In one embodiment, the oral dosage form comprises:
(a) 250 mg of a supercritical $CO_2$ hops extract from the cultivar Pacific Gem
(b) approximately 250 mg canola oil
(c) 1 mg rosemary oil and
(d) optionally silicon dioxide
wherein the oral dosage form is a Capsugel DRcaps capsule.

In one embodiment, the oral dosage form comprises:
(a) 100 mg of a supercritical $CO_2$ hops extract from the cultivar Pacific Gem
(b) approximately 400 mg canola oil
(c) 1 mg rosemary oil and
(d) optionally silicon dioxide
wherein the oral dosage form is a Capsugel Licaps capsule.

In one embodiment, the oral dosage form comprises:
(a) 250 mg of a supercritical $CO_2$ hops extract from the cultivar Pacific Gem
(b) approximately 250 mg canola oil
(c) 1 mg rosemary oil and
(d) optionally silicon dioxide
wherein the oral dosage form is a Capsugel Licaps capsule.

The oral dosage form may be used to reduce energy intake in a subject, for reducing appetite, for increasing satiety hormones, for weight management, for appetite control, for decreasing food intake, for inducing satiety and/or for treating obesity in a subject.

In one embodiment, the invention therefore provides a method of reducing energy intake by a subject, comprising administering an oral dosage form according to the invention to the subject.

In one embodiment, the invention provides a method of reducing appetite, for increasing satiety hormones, for weight management, for appetite control, for decreasing food intake, for inducing satiety, and/or for treating obesity in a subject, comprising administering an oral dosage form according to the invention to the subject.

In one embodiment, the invention provides a method of losing weight (effecting weight loss) comprising administering an oral dosage for according to the invention to a subject. In one embodiment, the subject loses weight through decreased energy intake and improved appetite control.

The oral dosage form is administered in an effective amount. A person skilled in the art can predict an effective amount from dose-response curves derived from in vitro or animal model tests. For example, an oral dosage form comprising 100 mg of Pacific Gem hops extract contains 51 mg (143 µM) of acids. This dose provides 20 mg or 57 µM of cohumulone and 31 mg or 85 µM of adhumulone/humulone. Assuming a gastric volume of 1 L, the dosing is above the EC50 concentrations determined from in vitro testing for pure compounds (~20 µM).

An effective amount of the hops extract will be about 10 mg to about 1000 mg of extract per day. A 10 mg to 1000 mg dose of a $CO_2$ Pacific Gem extract corresponds to about 2 to 200 mg of cohumulone and about 5 to 500 mg of alpha acids. In one embodiment, an effective amount of the hops extract will be about 20 mg to about 800 mg of extract per day. A 20 mg to 800 mg dose of a $CO_2$ Pacific Gem extract corresponds to about 4 to 160 mg of cohumulone and about 10 to 400 mg of alpha acids. In one embodiment, an effective amount of the hops extract will be about 50 mg to about 500 mg of extract per day. A 50 mg to 500 mg dose of a $CO_2$ Pacific Gem extract corresponds to about 10 to 100 mg of cohumulone and about 25 to 250 mg of alpha acids. In one embodiment, an effective amount of hops extract is about 100 mg to about 200 mg per day. A 100 mg to 200 mg dose of a $CO_2$ Pacific Gem extract corresponds to about 20 to 40 mg of cohumulone and about 50 to 100 mg of alpha acids. The effective amount may be either a single daily dose or divided doses throughout the day. For example, in one embodiment a subject may take two dosage forms comprising 100 mg of hops extract per day. In another embodiment, a subject may take two dosage forms comprising 250 mg of hops extract per day.

In one embodiment the oral dosage form is administered to the subject before an eating occasion. In one embodiment the oral dosage form is administered at least 30 minutes before an eating occasion. In one embodiment the oral dosage form is administered at least 45 minutes or one hour before an eating occasion. In one embodiment the oral dosage form is administered between one and three hours before an eating occasion. In one embodiment the oral dosage form is administered to the subject about one hour before an eating occasion. An eating occasion may be a main meal ie, breakfast, lunch or dinner, or any another time during the day where the subject expects to eat eg, morning tea or supper, or when the subject is prone to unnecessary eating eg, snacking after dinner or mid-afternoon.

In one embodiment the oral dosage form may be used to support a diet or intermittent fasting protocol. In this context, intermittent fasting means an eating pattern that cycles between periods of fasting and eating and where the fasting periods are longer than usually occurs with conventional eating patterns (eg, breakfast, lunch and dinner). An example of an intermittent fasting protocol is the 5:2 diet, where subjects fast, or eat very limited calories, for two days each week. The oral dosage form can be used on the two calorie limited days of the week to suppress appetite. Other examples of intermittent fasting protocols include protocols with different numbers of fasting days for example, alternate day fasting or fasting one day a week. Another example of intermittent fasting is where a subject fasts or eats very limited calories for one week of every month. Another example of intermittent fasting is a regularly scheduled fasting period within a day, for example extended overnight fasting (eg, the 16:8 protocol) or not eating before or after a certain time each day.

In one embodiment the oral dosage form may be used to extend a period of fasting. For example, in one embodiment the oral dosage form may be used to extend the period of time before a subject is hungry enough to eat, or to suppress appetite during any period of fasting, or to reduce appetite to avoid eating outside of designated meal times. Each dosage may remain effective for up to four to five hours.

In one embodiment, 100 mg of extract is administered to the subject prior to each eating occasion. In one embodiment a subject may have five eating occasions per day. For example, three meals, one snack, and one supplemental use.

In one embodiment, an oral dosage form comprising 250 mg of hops extract is administered to the subject once or twice a day.

In one embodiment, an oral dosage form comprising 100 mg of hops extract is administered to the subject once or twice a day.

In one embodiment the invention relates to the use of a supercritical $CO_2$ hops extract from the cultivar Pacific Gem in the manufacture of a medicament for reducing energy intake, for reducing appetite, for increasing satiety hormones, for weight management, for appetite control, for decreasing food intake, for inducing satiety, and/or for treating obesity. In one embodiment the medicament is in the form of a Capsugel DRcaps capsule. In one embodiment the medicament is in the form of a Capsugel Licaps capsule. In one embodiment the capsule contains an oil formulation comprising the hops extract, an edible oil, an antioxidant and optionally silicon dioxide as discussed above. In one embodiment the capsule contains an oil formulation comprising the hops extract, an edible oil and an antioxidant as discussed above.

In one embodiment, the invention provides a method of reducing energy intake by a subject comprising administering an agent capable of binding TAS2R1, TAS2R14 and TAS2R40 in the gastrointestinal tract of the subject. In one embodiment the agent is a hops extract as described above. In another embodiment the agent is an oral dosage form of the invention.

In one embodiment, the invention provides a method of reducing energy intake by a subject comprising administering a hops extract to the subject, wherein the acid component of the hops extract is not isomerised. In one embodiment the hops extract is formulated as an oral dosage form of the invention.

In one embodiment, the invention provides a method of extending a period of fasting comprising administering a hops extract to the subject. In one embodiment the hops extract is formulated as an oral dosage form of the invention.

In one embodiment, the invention provides a method of reducing appetite during a period of fasting comprising administering a hops extract to the subject. In one embodiment the hops extract is formulated as an oral dosage form of the invention.

Various aspects of the invention will now be illustrated in non-limiting ways by reference to the following examples.

EXAMPLES

General Protocol

Unless otherwise stated, the following general protocol was followed.

Example 1: Hops Responsive TAS2R in the Gut

Gut biopsy samples were taken from 28 subjects. Five or 10 regions of the gut were sampled for each subject using either gastroscopy or colonoscopy. The regions sampled using gastroscopy were the gastric fundus, gastric body, gastric antrum, D2 duodenum and proximal jejunum. The regions sampled using colonoscopy were the terminal ileum, ascending colon transverse colon, sigmoid colon and rectum.

A total of 15 samples (from different individuals) were collected from all regions save the proximal jejunum, where 14 were collected as one sample failed post processing quality control.

Analysis of the sample was done by NanoString nCounter gene expression assay. A detection cut off of 50 counts was chosen based on the highest values in the negative control samples as well as also being greater than the average of the negative controls plus 2 standard deviations.

TAS2R14 was present in all samples (149/149). TAS2R40 was present in most samples (128/149). TAS2R1 was present in some samples (14/149).

At an individual subject level, all subjects had TAS2R14 and TAS2R40 present in at least one of the sampled regions. However, only four of the 28 subjects had TAS2R1 in at least one of the sampled regions.

Example 2: Hops Extract

Supercritical $CO_2$ Pacific Gem hop extract was sourced from NZ Hops.

The chemical composition of the supercritical $CO_2$ hops extract was determined by LCMS. The method used was that described in European Brewery Convention. 1998. Iso α-, α- and β-acids in hop and isomerized hop extracts by HPLC. Section 7 Method 7.8, p. 1-4. In EBC analysis Committee (ed.), Analytica-EBC, 5th ed. Verlag Hans Carl Getranke-Fachverlag: Nurnberg, Germany. 7. European Brewery Convention. 1998. The chemical composition was: alpha acids (50.99%) comprising cohumulone (20.03%) and adhumulone/humulone (30.96%); Beta acids (29.45%) comprising colupulone (20.25%) and adlupulone/lupulone (9.20%). Trace amounts of xanthohumol (0.07%), a prenylated chalconoid, were also detected.

Example 3: A Comparison of High Alpha Acid and Low Alpha Acid Hops Extracts

High alpha acid (Pacific Gem) and low alpha acid (Wai-iti) hops were sourced from NZ hops. Hops extracts were produced using an ethanol extraction based method that had an additional sugar removal step. A 7.5 g sample of freeze-dried, ground hops was placed in a 125 mL Schott bottle with 75 mL of extraction solution (ethanol/water/1M HCl=80:19:1; degassed and saturated with nitrogen). The mixture was homogenized (using an Ultra Turrax) for two minutes, then residue was rinsed off the Ultra Turrax into the bottle with a small amount of fresh extraction solution. The Schott bottle was flushed with nitrogen then capped and shaken overnight on an orbital shaker/roller for approximately 18 hours, covered with foil to reduce exposure to light and at ambient temperature. The resulting suspension was centrifuged at 10000 rpm for five minutes at room temperature. The supernatant was transferred to a clean 250 mL round bottomed flask and 0.5 g of Waters Oasis™ gel was added. The sample was taken down as near to dryness as practicable using reduced pressure on a rotary evaporator (water bath at ~25° C.), with the flask covered with aluminium foil to reduce the light. The drying process was completed using the freeze drier. The flask was reweighed and the mass of the crude sample is calculated. The flask was flushed with nitrogen, sealed with a plastic stopper and stored at −20° C. until ready for the fractionation step.

For the fractionation step, a Waters Oasis™ SPE cartridge (20 cc, 1 g) was prepared by conditioning it with 5 mL of methanol (degassed and saturated with nitrogen) followed by 10 mL of double-RO water (degassed and saturated with nitrogen), using the vacuum manifold.

The sample-coated Oasis™ gel was slurried with water (15 mL) and left to hydrate for 10 min. The slurry was then applied to the top of the pre-conditioned SPE cartridge. The vacuum manifold was used to draw the slurry down onto the packing in the cartridge.

The SPE cartridge was washed with 75 mL of double-RO water (degassed and saturated with nitrogen) to remove endogenous sugars (for small fruits and samples high in sugars, use 150 mL) and the water washings put aside.

The phenolic material was eluted with methanol (50 mL, degassed and saturated with nitrogen), and the eluent collected into a tared 100 mL round-bottomed flask. The solvent was removed under reduced pressure on a rotary evaporator and the drying process was completed using a freeze drier. The tared flask was reweighed and the mass of the isolated phenolic material calculated.

The dried material was redissolved in 15 mL of methanol (degassed and saturated with nitrogen) and 1 mL aliquots pipetted out into each of 15 Eppendorf tubes (each tube therefore contained the phytochemicals present ~500 mg of dried hops material). The solvent was removed under reduced pressure on the Labconco (Kansas, US) Centrivap concentrator, and each tube stored at −20° C. until required.

The capacity for hops extracts to activate bitter taste receptors was assessed using intracellular calcium concentrations [Ca2+]i as a marker of both Tas2R activation and appetite suppressing hormone release. A screening assay was carried out to compare the effects of high alpha acid and low alpha acid hops extracts on intracellular calcium in Hutu80 enteroendocrine cells. The acid composition of the high alpha acid hops was alpha acid (13.9%), beta acid (7.4%). The acid composition of the low alpha acid hops was alpha acid (2.7%) beta acid (5.0%).

Figure 1:
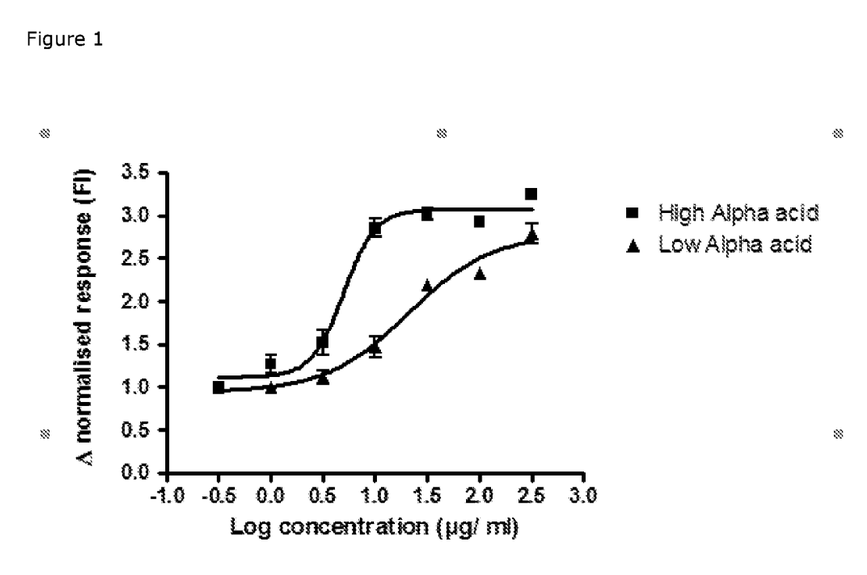
FIG. 1 shows the relative change in intracellular calcium in Hutu80 enteroendocrine cells at 5 min following the addition of either a high alpha acid (Pacific Gem, 13.9%) or low alpha acid (Wai-iti, 2.7%) hops extract.

An $EC_{50}$ dose response showing the relative change in intracellular calcium in Hutu80 enteroendocrine cells at 5 min following the addition of either a high alpha acid (Pacific Gem, 13.9%) or low alpha acid (Wai-iti, 2.7%) hops extract is shown in FIG. 1 and Table 1. The high alpha acid extract was shown to be significantly more effective at stimulating bitter taste receptor signalling in human enteroendocrine cells than the low alpha acid extract. The greater capacity of the Pacific gem extract to induce bitter taste receptor signalling demonstrates that the alpha acids are primary mediator of this bioactivity and further that hops extracts higher in alpha acids would stimulate greater release of appetite supressing peptide hormones.

TABLE 1

| Hops | EC 50 (µg/ml) |
|---|---|
| High alpha acid | 5 |
| Low alpha acid | 21 |

Example 4: Fractionation and Isolation of Cohumulone and Adhumulone/Humulone

A Pacific gem hop extract was coated onto 3 g C18 (Aldrich octadecyl-functionalized silica gel) by rotary evaporating at 30° C. and applied to the pre-conditioned 5 g C18 Isolute SPE cartridge preconditioned with EtOH, 1:1 EtOH:H2O, H2O (10 ml).

This was eluted with 2×10 ml of 50:50 EtOH:H2O, 60"40 EtOH:H2O, EtOH, 70"30 EtOH:H2O, EtOH, 80"20 EtOH:H2O, EtOH, 90"10 EtOH:H2O, EtOH and EtOAc to give 16 10 ml fractions.

Fraction 5-8 (965 mg), contained a concentration of the target compounds, xanthohumol and the alpha and beta bitter acids. These were identified by both HPLC and TLC using a mobile phase of heptane (85%), isopropyl alcohol (14.5%) and formic acid (0.5%). The bands were visualised using a Fe (III) dip (10% FeCl3 in H2O).

Xanthohumol produced an orange visual band TLC Rf=0.22 and HPLC RT 37.1 min. The alpha bitter acids produce a visible blue band after treatment. Rf=0.36 (RT 38.1-38.3 min); and the beta bitter acid produced a visible red band. Rf=0.46 (RT 38.6-38.8 min).

A portion of the bitter acid fraction (100 mg) was taken up in methanol (1.9 ml) and subjected to RP semi preparative chromatography using Phenomenex Luna 5 µm, C18 (2) 100 Å, 250×10 mm column with a Merck LlChrospher 100 RP-18 e (5 µm) guard fitted. This used a temperature of 30° C., mobile phase 90:10 methanol (HPLC grade), $H_2O$ (Milli Q) containing 2.5% formic acid and a flow rate of 4.5 ml/min and monitored at 370 nm.

Figure 2:
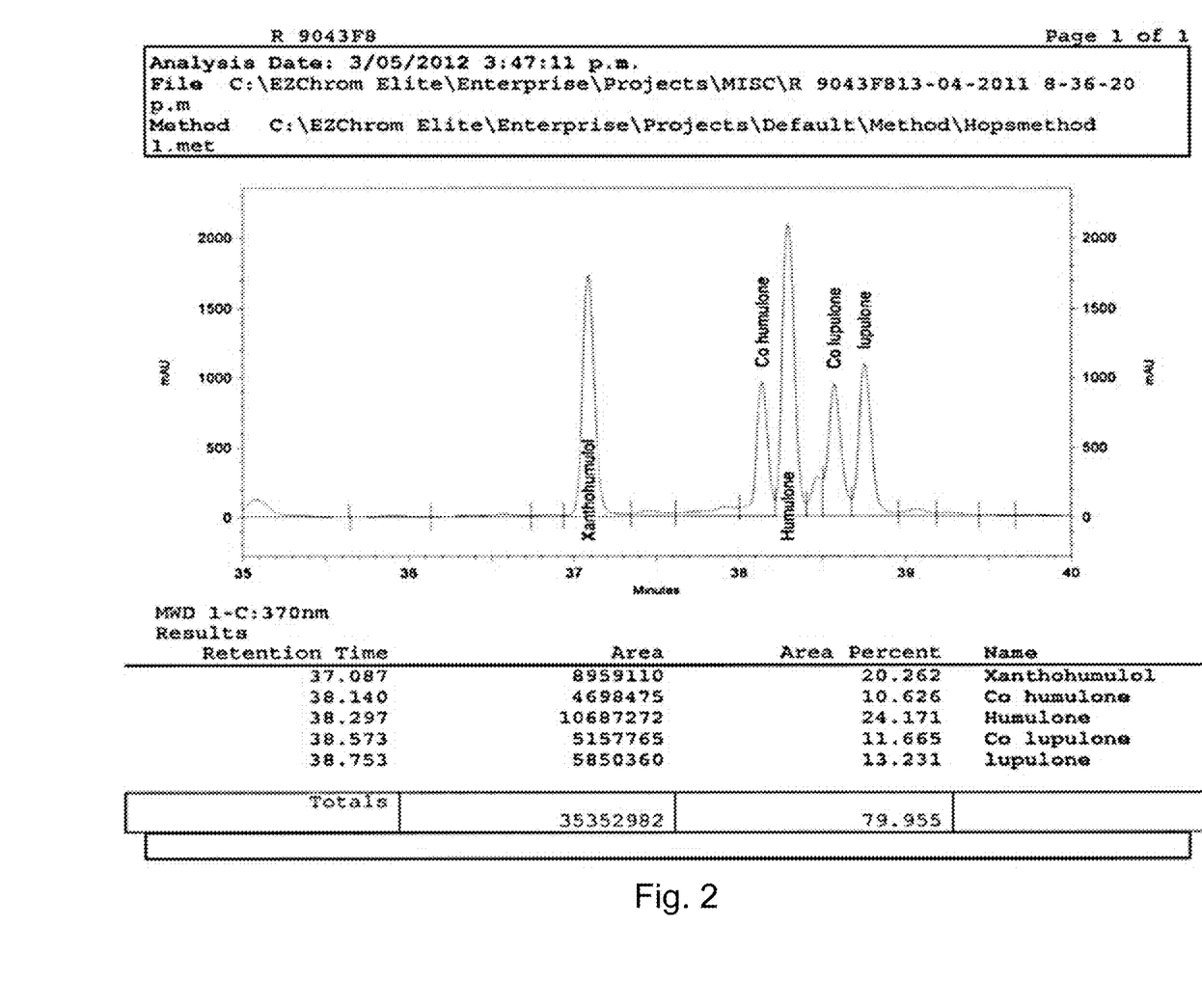
FIG. 2 shows the isolation of cohumulone, humulone plus adhumulone, colupulone and lupulone plus adlupulone from a Pacific Gem hops extract.

Four fractions were collected as shown in FIG. 2 and identified as cohumulone (RT 38.1 min), humulone plus adhumulone (RT 38.3 min), colupulone (RT 38.6 min) and lupulone plus adlupulone (RT 38.8 min) by TLC and confirmed by $^1$H NMR. (Schlotterbeck & Bayer 1996).

Example 5: Hutu-80 Response to Pure Acids

Hutu-80 responses to a Pacific gem hops extract and pure hops alpha and beta acids was determined in an assay screening system. The alpha acids tested were cohumulone and adhumulone/humulone (not discriminated by the analysis technique). The beta acids were colupulone and adlupulone/lupulone (not discriminated by the analysis technique).

To prepare the fractionated sample, Pacific Gem hop extract was coated onto 3 g C18 (Aldrich octadecyl-functionalized silica gel) by rotary evaporating at 30° C. and applied to the pre-conditioned 5 g C18 Isolute SPE cartridge preconditioned with EtOH, 1:1 EtOH:H2O, H2O (10 ml).

This was eluted with 2×10 ml of 50:50 EtOH:H2O, 60"40 EtOH:H2O, EtOH, 70"30 EtOH:H2O, EtOH, 80"20 EtOH:H2O, EtOH, 90"10 EtOH:H2O, EtOH and EtOAc to give 16 10 ml fractions.

Fraction 5-8 (965 mg), contained a concentration of the target compounds, the alpha and beta bitter acids.

These were identified by both HPLC and TLC using a mobile phase of heptane (85%), isopropyl alcohol (14.5%) and formic acid (0.5%). The bands were visualised using a Fe (III) dip (10% FeCl3 in H2O).

The alpha bitter acids produce a visible blue band after treatment. Rf=0.36 (RT 38.1-38.3 min); and the beta bitter acid produced a visible red band. Rf=0.46 (RT 38.6-38.8 min).

A portion of the bitter acid fraction (100 mg) was taken up in methanol (1.9 ml) and subjected to RP semi preparative chromatography using Phenomenex Luna 5 μm, C18 (2) 100 Å, 250×10 mm column with a Merck LlChrospher 100 RP-18 e (5 μm) guard fitted. This used a temperature of 30° C., mobile phase 90:10 methanol (HPLC grade), $H_2O$ (Milli Q) containing 2.5% formic acid and a flow rate of 4.5 ml/min and monitored at 370 nm.

Six fractions were collected and identified by HPLC and $^1$H NMR. (Schlotterbeck & Bayer 1996) (Table 1) as cohumulone+humulone, cohumulone, humulone plus adhumulone, colupulone and lupulone plus adlupulone.

Activation of human TAS2Rs receptors was measured by monitoring variations in intracellular $Ca^{2+}$ concentrations ($[Ca^{2+}]i$) using a Flurostar Omega (BMG LABTECH, Germany) (excitation 485 nm/emission 520 nm).

Hutu-80 cells (Cat #HTB-40, ATCC Manassas, Va.) were seeded in supplemented MEM (Cat #11095-080, Thermo Fisher, Walthan, Mass.) into Poly-Lysin-coated 96-well black wall, clear bottom plates (Cat #356640, Corning Inc. New York) at a density of 3.5×10 5 cells/ml, 100 μl/wel, cultured overnight and then loaded with the $Ca^{2+}$-sensitive fluorescent dye Fluo 4-AM (Cat #F14201, Thermo Fisher, Walthan, Mass.), following suppliers guidelines. The dye loading medium composition was: 0.02% Pluronic F-127 (Cat #P6866 Thermo Fisher, Walthan, Mass.), 0.2 μM Sulfinpyrazone (Cat #S9509, Sigma, St. Louis, Mo.), and 2.5 μM Fluo 4-AM in Hanks Buffered Saline Solution (Cat #14025092, Thermo Fisher, Walthan, Mass.).

Compounds to test were prepared in DMSO (Cat #D8418, Sigma, St. Louis, Mo.) and transferred onto the cells immediately prior to commencing of the assay measurements. To obtain a baseline, fluorescence signals (excitation 485 nm/emission 520 nm) were measured immediately before the addition of compounds on the cells.

The change in intracellular calcium in Hutu80 enteroendocrine cells was measured at 5 min following the addition of purified hops acids at doses of 200, 63.2, 20, 6.32, 2, 0.632, 0.2 and 0 μM.

Figure 3:
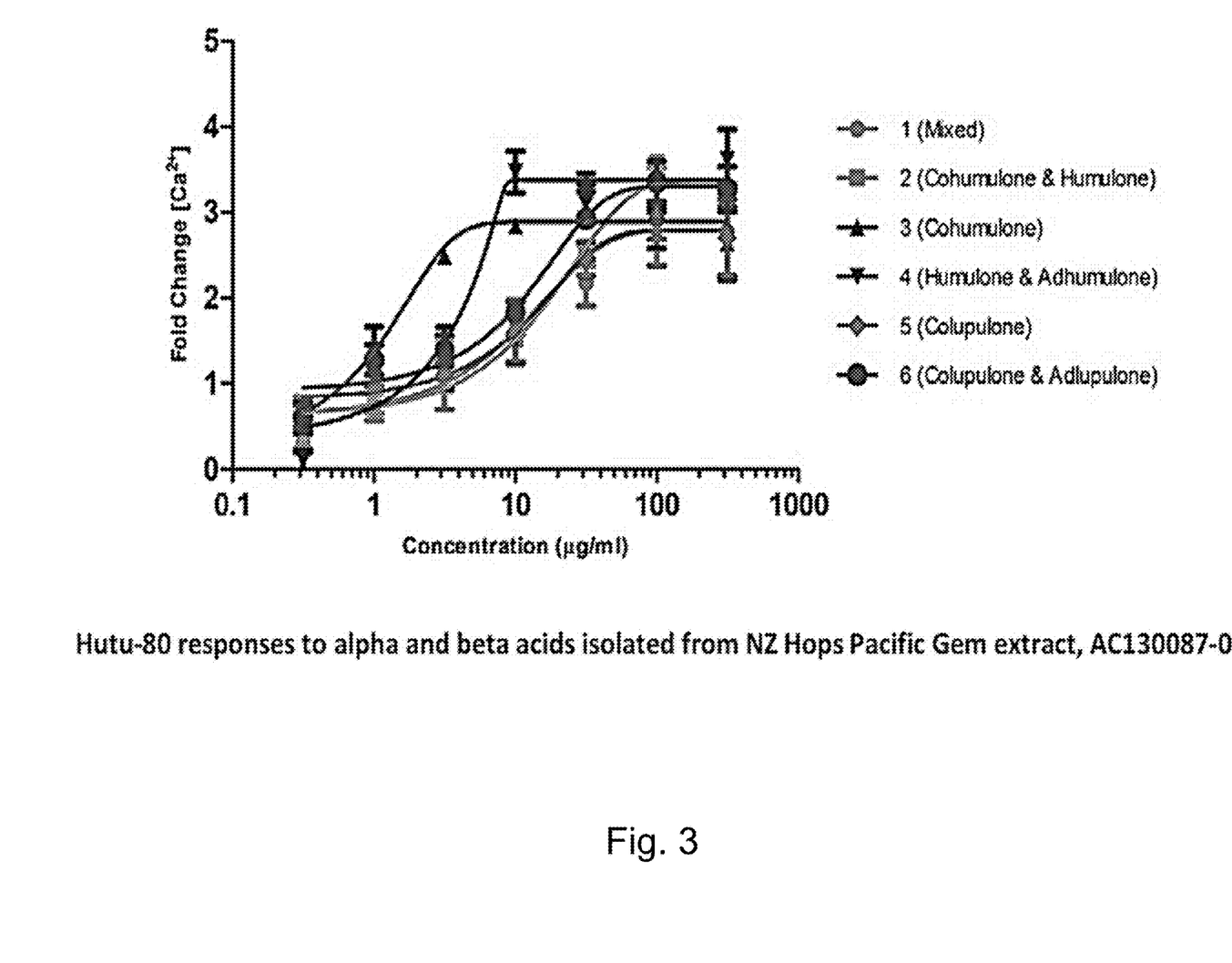
FIG. 3 shows the relative change in intracellular calcium in Hutu80 enteroendocrine cells at 5 min following the addition of purified hops acids at doses of 200, 63.2, 20, 6.32, 2, 0.632, 0.2 and 0 μM.

The results are shown in FIG. 3 and Table 2. Hops acid enriched pacific gem extract (1) and isolated alpha and beta acids (2-6) stimulated bitter taste receptor (Tas2R) signalling in human enteroendocrine cells line Hutu-80. Activity was shown in all fractions evaluated, with the alpha acid cohumulone showing activity at the lowest concentration (3) followed by the mixed sample containing other alpha acids humulone and adhumulone (4).

TABLE 2

| Hops | EC 50 (μg/ml) |
| --- | --- |
| Pacific gem hops extract | 5.923 |
| Cohumulone and humulone | 17.03 |
| Cohumulone | 1.153 |
| Humulone and adhumulone | 3.542 |
| Colupulone | 12.72 |
| Colupulone and adlupulone | 11.61 |

These results suggest that the alpha acids, in particular cohumulone, are the most potent activators of Tas2R signalling in intestinal enteroendocrine cells, although activity is still present in beta acid samples.

The result for cohumulone and humulone is surprisingly high. The inventors believe this may be due to a sampling error. If activity is primarily through TAS2R40, then it would be expected that a fraction that was mostly humulone would have much lower activity than a fraction that had a large amount of adhumulone or cohumulone.

Example 6: Formulation of an Oral Dosage Form

Supercritical $CO_2$ Pacific Gem hop extract was sourced from NZ Hops. Cold pressed, GE free, canola (rapeseed) oil was sourced from Pure Oil NZ. Capsules were size 0 DRcaps capsules from Capsugel (USA). All other chemicals and reagents were standard laboratory supplies.

An oral dosage form was produced by dissolving a Pacific Gem $CO_2$ extract comprising 255 mg (714 μM) of total alpha acids in 250 μL of canola oil, a 2:1 V/V ratio of hops extract to canola oil. This dose provides 100 mg or 287 μM of cohumulone and 155 mg or 427 μM of adhumulone/humulone. The mixture was then stirred with a plastic rod until a homogeneous suspension was obtained. During use, the suspension was stirred gently every 5 minutes to maintain homogeneity.

The oil and hops suspension was divided in two, and each portion was manually filled into size 0 DRcaps capsule using a pipette. The accuracy of delivery by this method was checked by weighing of replicate pipetting's. The capsules were pressed together.

The profile of the extract used in the formulation is provided in Table 3.

Example 7: In Vivo GI Tract Hormone Activity of Hops Extracts, Gastric Vs Duodenal Release Twenty healthy lean (BMI=23.5±0.3 kg/m2) male volunteers participated in a randomised three-treatment, double-blind, cross-over study with a 1 week washout between treatments. Overnight-fasted participants were cannulated and provided with a standardised 2 MJ Breakfast (t=−120, 0900 h). Treatments (500 mg hops extract or placebo) were administered in DRcaps (Capsugel, USA) (t=0, 1100 h) or Vcaps®, (Capsugel, USA) (t=30, 1130 h) for targeted duodenal or gastric release, respectively. The DRcaps were produced according to the method outlined in Example 6. To provide 500 mg hops extract, two capsules were administered to the subject. To maintain treatment blinding, placebo capsules were also administered as part of each treatment.

Energy intake was recorded at an ad libitum lunch (t=60, 1200 h) and snack (t=180, 1400 h). Blood samples and visual analogue scale (VAS) subjective ratings of appetite were taken throughout the day. CCK concentrations were measured by RIA (Eurodiagnostica) and GLP-1, PYY, and Ghrelin concentrations by multiplex assay (Merckmillipore). Data were analysed using residual maximum likelihood (REML) (SAS: PROC MIXED, SAS version 9.4). Where the residual maximum likelihood was significant, Tukey's post hoc analysis was used for comparisons between treatments. Results are presented as means+s.e.m.

19 participants completed the study with one participant excluded for failure to follow the protocol. Baseline characteristics of trial participants are shown in Table 4. All measurements were recorded at screening visit.

Reported adverse events are shown in Table 5 with most reported side effects associated with gastric delivery of the hops extract.

Figure 4:
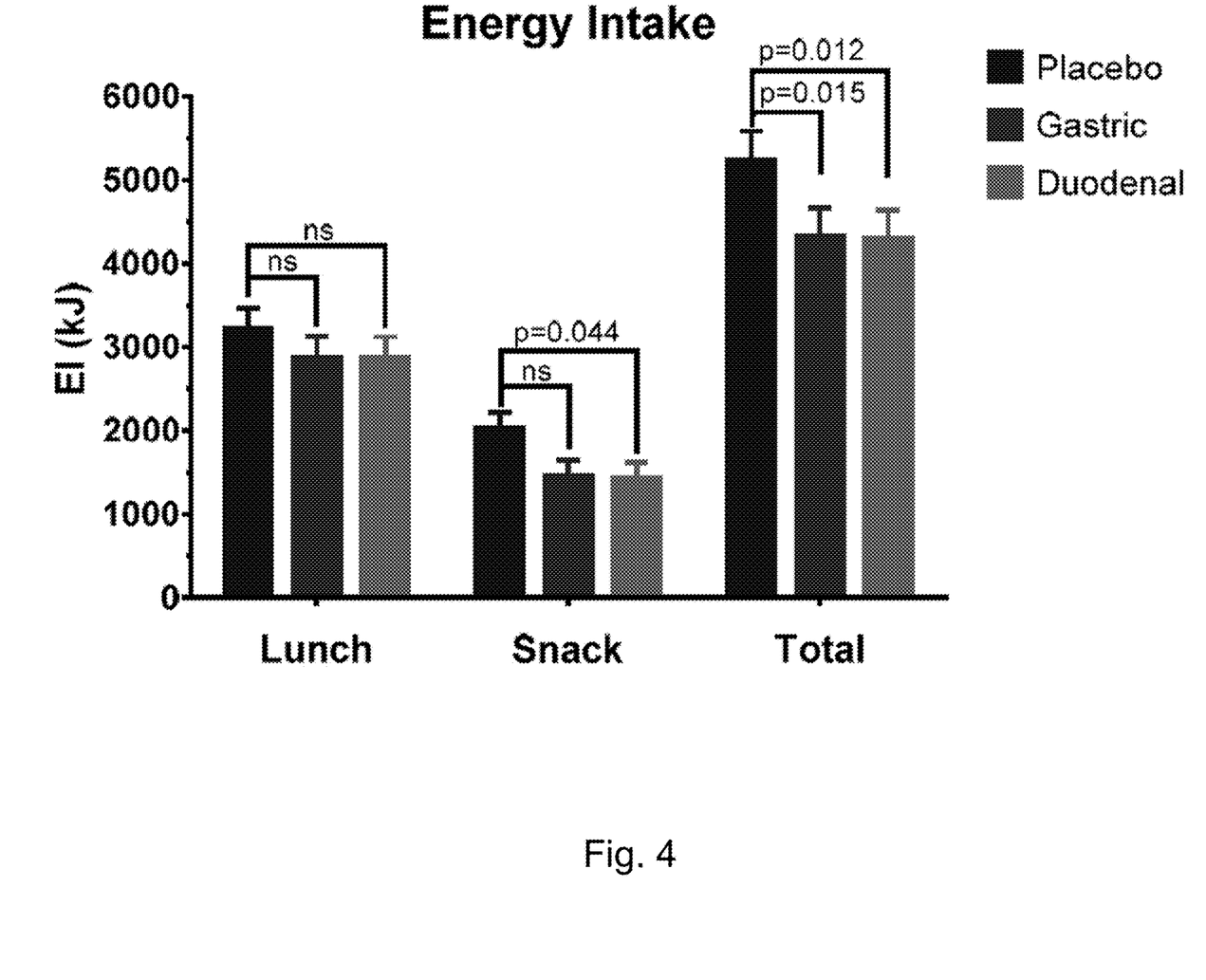
FIG. 4 shows the energy intake (kJ) at lunch and snack Ad libitum meals and combined (total) for subjects administered an oral dosage form according to the invention or a placebo.

A significant main effect of treatment for ad libitum meal energy intake (EI) was observed at the snack $F(2,34)=4.03$, $p=0.027$ and lunch+snack (Total) $F(2,34)=6.04$, $p=0.006$ but not the lunch (FIG. 4). Duodenal delivery of hops extract significantly reduced EI by $595\pm237$ kJ ($p<0.05$) at the ad libitum snack. While both gastric and duodenal delivery of hops extract significantly reduced total (lunch+snack) EI by $911\pm308$ kJ and $944\pm309$ kJ, respectively.

tive side effects were reported with the DRcaps capsules. Capsule type also had an effect on hormonal responses.

TABLE 6

| Hormone response | | |
|---|---|---|
| Hormone | Main Treatment effect | Treatment × Time Interaction |
| Ghrelin | $F(2, 33.1) = 0.26, p = 0.771$ | $F(30, 440) = 1.74, p = 0.010$ |
| CCK | $F(2, 70.1) = 5.8, p = 0.005$ | $F(30, 481) = 1.86, p = 0.004$ |
| GLP-1 | $F(2, 33) = 2.02, p = 0.148$ | $F(30, 422) = 1.53, p = 0.038$ |
| PYY | $F(2, 34.8) = 7.64, p = 0.002$ | $F(30, 475) = 1.51, p = 0.042$ |

Example 8: In Vivo Activity of an Oral Dosage Form According to the Invention

Oral dosage forms were produced comprising 100 mg of a supercritical $CO_2$ hops extract from the cultivar Pacific Gem, approximately 492 mg canola oil, 1 mg rosemary oil and silicon dioxide. The oral dosage form was a Capsugel DRcaps capsule. These capsules were provided to three subjects.

TABLE 3

| | Xanthohumol % | Cohumulone % | Adhumulone % | Colupulone % | Alupulone, % | Alpha, % | Beta, % | % alpha as cohumulone | % beta as colupulone | Alpha:beta ratio |
|---|---|---|---|---|---|---|---|---|---|---|
| NZ Hops Pacific Gem extract, AC130087-0 | 0.07 | 20.03 | 30.96 | 20.25 | 9.20 | 50.99 | 29.45 | 39.29 | 68.76 | 1.73 |

TABLE 4

| Participants | | | |
|---|---|---|---|
| | Mean | SD | Range |
| Randomised into the trial | n = 20 | | |
| Completed all 3 treatments | n = 19 | | |
| Age (years) | 28.9 | 10.4 | 18-54 |
| Weight (kg) | 76.1 | 8.3 | 60.4-94.5 |
| Height (m) | 1.80 | 0.08 | 1.66-1.95 |
| BMI (kg/m$^2$) | 23.5 | 1.4 | 20.9-25.0 |

TABLE 5

| Side effects profile- Reported Adverse Events | | | |
|---|---|---|---|
| Adverse Event | Placebo | Gastric | Duodenal |
| Nausea | — | 2/19 mod-severe | — |
| Loose Stool | — | 6/19 mild-mod | — |
| Stomach rumbling | — | 1/19 mild | — |
| Upset Stomach | — | 1/19 (mild) | — |
| Bloating | — | 2/19 mod-severe | — |
| Headache | — | 1/19 mild | — |
| Lower Stool Frequency - following week | — | — | 1 (moderate) |

Figure 5:
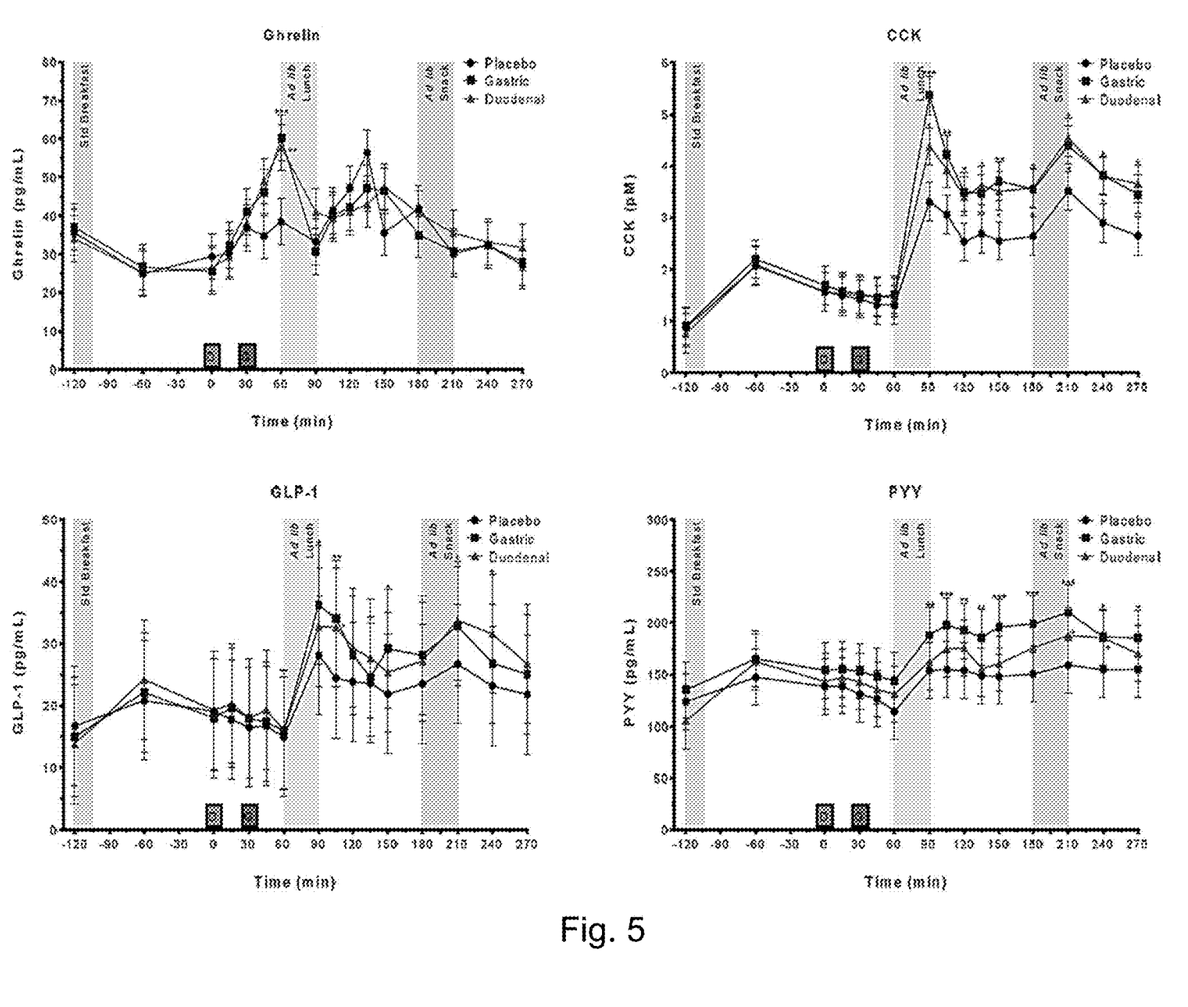
FIG. 5 shows the gut peptide hormone responses for subjects administered an oral dosage form according to the invention or a placebo.

Compared with placebo, both gastric and duodenal delivery of the hops extract stimulated significant increases in the gut peptide hormones Ghrelin, CCK, GLP-1 and PYY (FIG. 5 and associated Table 6).

The results show that the subject's energy intake was similar for both capsule types, but significantly fewer nega- One subject took one capsule "at lunch" and a second capsule "before dinner" five days a week. After six months of following this regimen, the subject had lost approximately 10 kilograms.

A second subject took one capsule at approximately 5 μm each work day, for approximately four months. During the treatment regimen the subject maintained her weight, despite the disruption caused to her usual diet and exercise regime caused by the Christmas holiday period. This subject reported significantly less snacking after work while following this regime. The subject also occasionally took at second dosage form before lunch and consider that she ate less calories at lunch on those occasions.

A third subject took one capsule daily at 4 μm for approximately 7 months. This subject also followed the 5:2 intermittent fasting diet and increased his physical activity. The subject lost approximately 11.5 kg during this time. The subject reported a suppressed appetite, and found taking the capsules assisted him with not eating dinner on his fasting days.

Example 9: In Vivo Activity of an Oral Dosage Form According to the Invention

Oral dosage forms were produced comprising 100 mg of a supercritical $CO_2$ hops extract from the cultivar Pacific Gem, approximately 492 mg canola oil, 1 mg rosemary oil and silicon dioxide. The oral dosage form was a Capsugel DRcaps capsule. These capsules were provided to approximately 30 subjects and subjects were invited to provide feedback on their experiences taking the oral dosage forms of the invention.

15 female subjects provided feedback. Of the 15 respondents, 12 reported a reduction in appetite after taking the oral dosage form and 10 considered the oral dosage forms were an effective tool for managing their weight. All 15 of the respondents reported that they had either lost or maintained their weight while taking the oral dosage forms. Of the four respondents that reported weight loss, the average amount of weight lost was 2.75 kg per person. The respondents reported taking the oral dosage forms in a number of ways, but most respondents took one or two oral dosage forms a day, usually before their regular meal times.

INDUSTRIAL APPLICABILITY

The oral dosage forms of the invention can be used as agents eg nutraceutical or pharmaceutical to help prevent, treat or manage conditions that are associated with obesity.

Those persons skilled in the art will understand that the above description is provided by way of illustration only and that the invention is not limited thereto.

What we claim is:

1. A delayed release oral dosage form comprising a hops extract, wherein the acid component of the hops extract is not isomerized, wherein the oral dosage form comprises a hydroxypropylmethyl cellulose (HPMC) capsule comprising:
   (a) 125 mg of a supercritical $CO_2$ hops extract from the cultivar Pacific Gem;
   (b) approximately 141 mg canola oil;
   (c) approximately 1 mg rosemary oil and; and
   (d) optionally a viscosity modifier.

2. The oral dosage form according to claim 1, wherein the hops extract comprises 25-100% w/w alpha-acids.

3. The oral dosage form according to claim 1, wherein the alpha acid component of the hops extract comprises 10-45% cohumulone.

4. The oral dosage form according to claim 1, wherein the oral dosage form comprises a viscosity modifier.

5. The oral dosage form according claim 1, wherein the contents of the oral dosage form has a viscosity between 250 cP and 8000 cP.

6. A method of
   (a) reducing appetite
   (b) increasing satiety hormones
   (c) weight management
   (d) appetite control
   (e) decreasing food intake
   (f) inducing satiety and/or
   (g) treating obesity
   comprising administering an oral dosage form according to claim 1 to the subject.

7. The method according to claim 6, wherein the oral dosage form is administered to the subject at least one hour before meal time.

8. The method according to claim 6, wherein the subject is following an intermittent fasting protocol.

9. The method according to claim 6, wherein the oral dosage form is administered to the subject during a period of fasting.

* * * * *